(12) United States Patent
Krawczyk et al.

(10) Patent No.: US 10,106,469 B2
(45) Date of Patent: Oct. 23, 2018

(54) UREA COMPOSITION AND METHOD FOR PRODUCING SAME

(71) Applicants: Uhde Fertilizer Technology B.V., NW Roermond (NL); ThyssenKrupp AG, Essen (DE)

(72) Inventors: Thomas Krawczyk, Dortmund (DE); Matthias Potthoff, Dortmund (DE); Luc Vanmarcke, Lembecke (BE); Erik Alexander Bijpost, Nieuwegein (NL); Alexander Maslow, Deventer (NL)

(73) Assignees: UHDE FERTILIZER TECHNOLOGY B.V., NW Roemond (NL); THYSSENKRUPP AG, Essen (DE)

( * ) Notice: Subject to any disclaimer, the term of this patent is extended or adjusted under 35 U.S.C. 154(b) by 0 days.

(21) Appl. No.: 15/320,269

(22) PCT Filed: Jun. 17, 2015

(86) PCT No.: PCT/EP2015/063599
§ 371 (c)(1),
(2) Date: Mar. 2, 2017

(87) PCT Pub. No.: WO2015/193377
PCT Pub. Date: Dec. 23, 2015

(65) Prior Publication Data
US 2017/0190632 A1 Jul. 6, 2017

(30) Foreign Application Priority Data
Jun. 20, 2014 (DE) .................. 10 2014 108 703

(51) Int. Cl.
| | |
|---|---|
| C05C 9/00 | (2006.01) |
| A61K 31/17 | (2006.01) |
| A61K 47/08 | (2006.01) |
| A61K 47/34 | (2017.01) |
| A61K 47/32 | (2006.01) |
| A61K 47/12 | (2006.01) |
| A61K 9/00 | (2006.01) |
| C08J 3/12 | (2006.01) |
| C05G 3/00 | (2006.01) |
| B01J 2/16 | (2006.01) |
| B01J 2/00 | (2006.01) |
| A23K 20/10 | (2016.01) |
| A23K 40/10 | (2016.01) |
| A23K 50/15 | (2016.01) |

(52) U.S. Cl.
CPC .............. *C05C 9/00* (2013.01); *A23K 20/10* (2016.05); *A23K 40/10* (2016.05); *A23K 50/15* (2016.05); *A61K 9/0056* (2013.01); *A61K 31/17* (2013.01); *A61K 47/08* (2013.01); *A61K 47/12* (2013.01); *A61K 47/32* (2013.01); *A61K 47/34* (2013.01); *B01J 2/003* (2013.01); *B01J 2/16* (2013.01); *C05C 9/005* (2013.01); *C05G 3/0058* (2013.01); *C08J 3/12* (2013.01); *C08J 2339/02* (2013.01); *C08J 2379/02* (2013.01); *C08J 2439/02* (2013.01); *C08J 2479/02* (2013.01)

(58) Field of Classification Search
None
See application file for complete search history.

(56) References Cited

U.S. PATENT DOCUMENTS

| | | | |
|---|---|---|---|
| 4,204,053 A | 5/1980 | Elstrom et al. | |
| 4,219,589 A | 8/1980 | Niks | |
| 5,766,302 A | 6/1998 | Lefroy et al. | |
| 2004/0009878 A1 | 1/2004 | Lynch et al. | |
| 2008/0041131 A1 | 2/2008 | Van Belzen et al. | |
| 2008/0190161 A1 | 8/2008 | van Belzen et al. | |

FOREIGN PATENT DOCUMENTS

| | | | |
|---|---|---|---|
| EP | 533024 A2 | 3/1993 | |
| FR | 1021100 A | 2/1953 | |
| FR | 2874008 A1 | 2/2006 | |
| JP | 2000044371 A | 2/2000 | |
| JP | 2012509833 A | 4/2012 | |
| WO | 2006091077 A1 | 8/2006 | |
| WO | WO 2006/091077 | * | 8/2006 |
| WO | 2010060535 | 6/2010 | |

OTHER PUBLICATIONS

Brosse et al. disclose in FR2874008 (2006) (Machine Translation).*
PCT Application PCT/EP2015/063599, International Search Report, dated Feb. 10, 2015, 3 pages.
PCT App. No. PCT/EP2015/063599, International Search Report dated Dec. 23, 2015, 32 pages.
Japanese Application No. 2016-574075, Office Action dated May 28, 2018, 10 pages.

* cited by examiner

*Primary Examiner* — Dennis Heyer
(74) *Attorney, Agent, or Firm* — Lathrop Gage L.L.P.

(57) ABSTRACT

Disclosed is a particulate, urea-containing composition, to a method and apparatus for producing it, to the use thereof as fertilizer, as technical urea or as feed additive, and to the use of an additive for producing a particulate, urea-containing composition.

13 Claims, No Drawings

UREA COMPOSITION AND METHOD FOR PRODUCING SAME

RELATED APPLICATIONS

This application is the national stage entry of International Patent Application No. PCT/EP2015/063599, filed Jun. 17, 2015, which designated the United States, and which claims priority to German patent Application No. 10 2014 108 703.8, filed Jun. 20, 2014. Each of these documents is incorporated by reference herein in their entireties.

BACKGROUND

1. Field of the Invention

The invention relates to a particulate, urea-containing composition, to a method and apparatus for producing it, to the use thereof as fertilizer, as technical urea or feed additive, and to the use of an additive for producing a particulate, urea-containing composition.

2. State of the Art

For the production of particulate, urea-containing compositions there are a variety of methods known in the prior art. Typically, in the past, urea particles have been produced by means of spray crystallization, in which a substantially water-free urea melt (water content of 0.1 to 0.3 wt %) are sprayed from the upper part of a spray crystallization tower into an ascending stream of air at ambient temperature, with the droplets solidifying to form crystals (prills). The prills obtained accordingly have relatively small diameters and also low mechanical strength.

Urea particles having larger diameters and better mechanical properties are nowadays usually produced by granulating a substantially water-free urea melt or an aqueous urea solution in a fluidized bed, as described in U.S. Pat. No. 4,219,589, for example. In these granulating methods, an aqueous urea solution having a urea concentration of 70-99.9 wt % is introduced in the form of very finely divided droplets having an average diameter of 20-120 µm into a fluidized bed of urea particles, the temperature being selected such that the water in the solution sprayed onto the urea particles is evaporated and urea is deposited on the particles, giving granules having a desired particle size of 2.5 mm or more.

Since this method produces relatively large quantities of fine dust, especially if the urea solution used has a water content of more than 5 wt %, it is common to use granulating additives which reduce this dusting. As a result of adding these additives, the granules and especially their surface remain plastic, and so, as a consequence of their rolling movements and of collisions, the particles obtained are round, with a smooth surface and good mechanical stability. The granules obtained accordingly therefore have high compressive strength and impact strength, a low propensity to form dust due to abrasion, and, moreover, only a low propensity toward caking even on prolonged storage. Such granulating additives are not employed only in fluidized bed granulation, however, but also in other methods, such as in spray crystallization or drum granulation, for example.

Granulation additives used are customarily formaldehyde and/or water-soluble adducts and/or condensation products of formaldehyde and urea, but they must be added in relatively large quantities and are not without problems in handling because of their toxic properties. Emissions of formaldehyde pose an acute health and environmental risk, despite such risks having been reduced by the introduction of urea-formaldehyde prepolymers such as UF80 or UF85. The issue of health risks also arises, moreover, in connection with the chronic exposure to formaldehyde vapors, which cannot be avoided entirely even by using such prepolymers.

Another problem associated with the granulation of urea is the production of dust, referring to particles having a diameter of less than 0.5 mm. This dust formation is attributable essentially to three sources. First, there is the abrasion of the granules owing to movements and collisions of the particles, in the fluidized bed, for example, where the amount of dust produced is dependent substantially on the mechanical properties of the granules. Furthermore, the nozzles in each case produce droplets having a certain distribution of diameters, with the finest droplets solidifying before they strike the urea particles, meaning that the dust thus formed leaves the granulator again together with the outgoing air. Lastly, a third source of dust is that obtained from the comminution of excessively large granules, which in the prior-art methods and plant are customarily passed straight back into the granulator. 10 to 20 wt % of the comminuted particles have a diameter of less than 1 mm, and a large proportion of this is dust. Accordingly, by way of this fraction of comminuted particles, 1 to 1.5% of dust per metric ton of end product is passed back into the granulator, and 3-5% of the total dust per metric ton of end product from an industrial plant is attributable to the granulator.

In order to prevent or alleviate the disadvantages identified above, a variety of alternatives to formaldehyde and its water-soluble adducts and/or condensation products have been investigated, but each of them is also hampered by restrictions and/or disadvantages.

One example is the use of alkali metal lignosulfonates, as described in U.S. Pat. No. 5,766,302, or the use of glyoxal or carbohydrates. In the resultant urea product, however, depending on the production method, these additives result in a yellowish or brownish coloration, which in many cases is undesirable, as in the case of the production of melamine, for example. On the other hand, the use of surface-active substances such as, for example, mixtures of polyvinyl acetate and polyvinyl alcohol as granulating additives leads likewise to problems, since these substances have a tendency to foam, as for example when the additive is mixed with the melt, or in the scrubbers, where the treated urea dust is dissolved and detrimentally affects the efficiency of the scrubbers. The tendency of the substances to form foam also has consequences for the end product, moreover, this product having a lower density and being rejected by the market. Overall, therefore, any tendency toward foaming is unacceptable in industrial application of the urea granules.

SUMMARY

Disclosed herein is a method for producing particulate, urea-containing compositions that does not have the disadvantages of the prior art, or at least has them in a reduced form.

DETAILED DESCRIPTION OF THE INVENTION

It has been found, surprisingly, that by using certain additives it is possible to obtain a urea-containing, particulate composition having satisfactory properties, without using formaldehyde and urea-formaldehyde condensates. In particular it is possible in this way:
- to avoid the health and environmental risks associated with the use of formaldehyde and urea-formaldehyde condensates; and/or
- to provide a more cost-effective alternative to producing the compositions, relative to compositions produced using formaldehyde and urea-formaldehyde condensates; and/or
- to reduce or even entirely avoid the unwanted coloration of the composition; and/or
- to reduce or even completely avoid the unwanted foaming during production or during wet scrubbing; and/or
- to achieve particle growth comparable with the use of formaldehyde and urea-formaldehyde condensates; and/or
- to reduce or even avoid completely the formation of dust during the production of the composition; and/or
- to obtain a particulate composition whose particles, in comparison to compositions produced using formaldehyde and urea-formaldehyde condensates, exhibit at least comparable or even improved properties, especially in respect of mechanical properties such as, for example, compressive strength, impact strength, low propensity toward abrasion or caking, particularly on prolonged storage.

One aspect of the invention relates to a particulate composition comprising (i) urea; and an additive comprising one or both of components (ii) and (iii): (ii) combination of at least one oligomer or polymer containing amino groups and at least one functionalized polyvinyl compound; and (iii) at least one aliphatic $C_2$-$C_8$ dialdehyde; where the weight fraction of component (i) is >60 wt % and the weight fraction of the sum of components (ii) and (iii) in the composition is <1 wt %.

Oligomers and polymers containing amino groups and employed in accordance with the invention comprise, in particular, polymers and oligomers having a molecular weight (MW) of 250 to 2 000 000, of 300 to 2 000 000, of 350 to 2 000 000, of 400 to 2 000 000, of 450 to 2 000 000, of 500 to 2 000 000, of 550 to 2 000 000, of 600 to 2 000 000, of 650 to 2 000 000, of 700 to 2 000 000, of 750 to 2 000 000, of 800 to 2 000 000, of 850 to 2 000 000, of 900 to 2 000 000, of 950 to 2 000 000, of 1000 to 2 000 000, of 1050 to 2 000 000, of 1100 to 2 000 000, of 1150 to 2 000 000, and of 1200 to 2 000 000 Daltons.

For example, the oligomers and polymers containing amino groups that are employed in accordance with the invention may have a molecular weight (MW) of 500 to 1 000 000, of 550 to 1 000 000, of 600 to 1 000 000, of 650 to 1 000 000, of 700 to 1 000 000, of 750 to 1 000 000, of 800 to 1 000 000, of 850 to 1 000 000, of 900 to 1 000 000, of 950 to 1 000 000, of 1000 to 1 000 000, of 1050 to 1 000 000, of 1100 to 1 000 000, of 1150 to 1 000 000, and also of 1200 to 1 000 000 Daltons, or in the range from 500 to 10 000, from 550 to 10 000, from 600 to 10 000, from 650 to 10 000, from 700 to 10 000, from 750 to 10 000, from 800 to 10 000, from 850 to 10 000, from 900 to 10 000, from 950 to 10 000, from 1000 to 10 000, from 1050 to 10 000, from 1100 to 10 000, from 1150 to 10 000, and from 1200 to 10 000 Daltons.

The oligomers and polymers containing amino groups may preferably have a nitrogen content of 10 to 50 wt %, based on the weight of the polymer or oligomer, and may contain primary, secondary or tertiary amino groups, independently of one another containing alkyl or arylalkyl groups, as for example $C_{1-6}$ alkyl or aryl-$C_{1-3}$ alkyl, where aryl may in particular be phenyl or pyridyl, which may be unsubstituted or, optionally, substituted by 1, 2, 3, 4 or 5 substituents selected independently of one another from the group consisting of F, Cl, Br, $CF_3$, $C_{1-6}$ alkyl, $C_{1-6}$ alkoxy, $NH_2$, $C_{1-6}$ alkylamino, and di($C_{1-6}$ alkyl)amino.

As oligomers and polymers containing amino groups, consideration is given, for example, to polyamines, polymeric polyamines, nitrogen-substituted vinyl polymers, polyoxazolines, polypropylenimine and its dendrimers, polyethylenimine and its dendrimers, polyamidoamine and its dendrimers, and also copolymers and derivatives and combinations of two or more of the stated substances.

Preferred oligomers and polymers containing amino groups comprise polyamines and polymeric polyamines, polyalkylenimines such as polyethylenimines and polypropylenimines, for example, polyvinylamines, polyalkoxylated polyamines, ethoxylated polyamines, propoxylated polyamines, alkylated and benzylated polyamines, and also combinations of two or more of the aforementioned components.

Especially preferred for use as oligomers and polymers containing amino groups are polyethylenimines, polyethylenimine dendrimers, and also their copolymers, derivatives, and mixtures of at least two of these components.

Suitable polyethylenimines may comprise linear or branched polyethylenimine polymers or oligomers having for example 10 or more monomer units, and also their derivatives, analogs, copolymers, and mixtures of at least two of these components.

Polyethylenimines may be obtained through the polymerization of ethylenimine, and are available commercially on the market, in the form, for example, of the Lupasol® and Epomin® product families and there, in particular, in the form of the products Lupasol® G20, Lupasol® FG, Lupasol® G35, Lupasol® P, and Lupasol® 1595 (the Lupasol® products are available from BASF (Florham Park, N.J., USA)), and also Epomin® SP-003, Epomin® SP-006, Epomin® SP-012, Epomin® SP-018, Epomin® SP-200, Epomin® SP-1000, and Epomin® SP-1050 (the Epomin® products are available from Nippon Shokubai (Osaka, Japan)).

Contemplated as functionalized polyvinyl compounds in accordance with the invention are, in particular, compounds based on the repeating unit $(CHXCHY)_n$, in which X is selected from the group consisting of H, $NH_2$, OH, COOH, COR, $CONH_2$, $CH_2NH_2$, $CH_2NHR$, $CH_2OH$, and $CH_2OR$, and Y is selected from the group consisting of $NH_2$, OH, COOH, COR, $CONH_2$, $CH_2NH_2$, $CH_2NHR$, $CH_2OH$, and $CH_2OR$, with R being able in each case, independently of any other, to be alkyl, more particularly $C_{1-6}$ alkyl, or aryl, more particularly phenyl or pyridyl, which may be unsubstituted or optionally substituted by 1, 2, 3, 4 or 5 substituents selected independently of one another from the group consisting of F, Cl, Br, $CF_3$, $C_{1-6}$ alkyl, $C_{1-6}$ alkoxy, $NH_2$, $C_{1-6}$ alkyl amino, and di($C_{1-6}$ alkyl)amino.

The functionalized polyvinyl compounds employed in accordance with the invention may for example have a molecular weight (MW) of 250 to 2 000 000, of 300 to 2 000 000, of 350 to 2 000 000, of 400 to 2 000 000, of 450 to 2 000 000, of 500 to 2 000 000, of 550 to 2 000 000, of 600 to 2 000 000, of 650 to 2 000 000, of 700 to 2 000 000, of 750 to 2 000 000, of 800 to 2 000 000, of 850 to 2 000 000, of 900 to 2 000 000, of 950 to 2 000 000, of 1000 to 2 000 000, of 1050 to 2 000 000, of 1100 to 2 000 000, of 1150 to 2 000 000, and also of 1200 to 2 000 000 Daltons.

A functionalized polyvinyl compound contemplated is preferably polyvinyl alcohol or polyvinylamine or a mixture thereof. With particular preference the functionalized polyvinyl compound is a polyvinylamine.

The polyvinylamine and the polyvinyl alcohol may each preferably have a molecular weight (MG) of 500 to 1 000 000, of 550 to 1 000 000, of 600 to 1 000 000, of 650 to 1 000 000, of 700 to 1 000 000, of 750 to 1 000 000, of 800 to 1 000 000, of 850 to 1 000 000, of 900 to 1 000 000, of 950 to 1 000 000, of 1000 to 1 000 000, of 1050 to 1 000 000, of 1100 to 1 000 000, of 1150 to 1 000 000, and also of 1200 to 1 000 000 Daltons, or in the range from 500 to 10 000, from 550 to 10 000, from 600 to 10 000, from 650 to 10 000, from 700 to 10 000, from 750 to 10 000, from 800 to 10 000, from 850 to 10 000, from 900 to 10 000, from 950 to 10 000, from 1000 to 10 000, from 1050 to 10 000, from 1100 to 10 000, from 1150 to 10 000, and also from 1200 to 10 000 Daltons.

Suitable polyvinylamines comprise, in particular, linear polymers and copolymers which derive from vinylformamide monomers and may comprise cationic and anionic polyvinylamine copolymers and also charged and protonated polyvinylamines.

Suitable polyvinylamines are available commercially on the market, examples being those of the Lupamin® product family, and there, more particularly, the products Lupamin® 1595, Lupamin® 4500, Lupamin® 5095, Lupamin® 9030, Lupamin® 9050, and Lupamin® 9095. Examples of cationic and anionic polyvinylamine copolymers are those of the Luredur® product family, and there more particularly the products Luredur® Am na, Luredur® AV, Luredur® VH, Luredur® VI, Luredur® VM, Luredur® PR8094, Luredur® PR8261, and Luredur® PR8349. Examples of charged or protonated polyvinylamines are products of the Catiofast® product series, and there more particularly the products Catiofast® GM, Catiofast® PL, Catiofast® PR8236, Catiofast® VCB, Catiofast® VFH, Catiofast® VLW, Catiofast® VMP, and Catiofast® VSH. The Lupamin®, Luredur®, and Catiofast® products are available from BASF (Florham Park, N.J., USA).

Employed as component (iii) of the invention are linear or branched aliphatic $C_2$-$C_8$ dialdehydes. Contemplated with preference as additive component (iii) is ethanedial or glutaraldehyde, more preferably glutaraldehyde.

Unless otherwise indicated, the weight figures (wt %) given in connection with the particulate composition are in each case always based on the total weight of the particulate composition. The skilled person recognizes that the specified components and weight figures need not be fulfilled for any fraction of the particles, however small, but instead must be fulfilled on average over a representative amount of the particles produced.

The particulate composition of the invention may comprise further constituents in addition to those stated. The nature of the constituents and also their amount are dependent, for example, on component (i) used. Thus the particulate composition of the invention may comprise water, in an amount for example of 0.05 to 0.5 wt %, more particularly 0.1 to 0.3 wt %, and may comprise byproducts of the synthesis of urea, such as biuret or $NH_3$, for example. The fraction of the byproducts is customarily not more than 1.5 wt %, more particularly not more than 1.25 wt %.

In one embodiment, the particulate composition comprises as component (iv) of the additive at least one compound selected from the group of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides, wherein preferably the weight fraction of component (i) is >60 wt % and the weight fraction of the sum of components (ii), (iii), and (iv) in the composition is <1 wt %.

The skilled person recognizes that the components (ii), (iii), and (iv) used may undergo partial or even complete interaction, optionally, with one another and optionally, also, with the urea component (i) during the production of the particulate composition. Known examples include crosslinking, with formation of covalent bonds for aldehydes and/or carboxylic anhydrides with urea, or the formation of complexes from urea and carboxylic acids. Components such as polyvinyl alcohol and polyvinylamine, for example, have a tendency to form hydrogen bonds. In the end product obtained, therefore, the components used for producing the particulate composition are optionally present in a partially or completely modified form. The invention also embraces modified components of this kind.

In another embodiment, the particulate composition of the invention comprises (i) urea; and an additive comprising component (ii) and one or both of components (iii) and (iv): (ii) combination of polyethylenimine and polyvinyl alcohol or combination of polyethylenimine and polyvinylamine; (iii) at least one aliphatic $C_2$-$C_8$ dialdehyde; and (iv) at least one compound selected from the group of aliphatic dicarboxylic acids, their salts and anhydrides, aliphatic tricarboxylic acids, their salts and anhydrides, aromatic dicarboxylic acids, their salts and anhydrides, and aldehydic acids, their salts and anhydrides; wherein preferably the weight fraction of component (i) is >97 wt % and the weight fraction of the sum of components (ii), (iii), and (iv) in the composition is <1 wt %.

Where the composition of the invention includes an aliphatic dicarboxylic acid as component (iv), this acid may preferably be selected from the group consisting of oxalic acid, malonic acid, succinic acid, glutaric acid, adipic acid, pimelic acid, suberic acid, azelaic acid, sebacic acid, undecanedioic acid, dodecanedioic acid, tridecanedioic acid, tetradecanedioic acid, hexadecanedioic acid, and also in each case their salts and anhydrides. Present with particular preference as dicarboxylic acid of component (iv) is oxalic acid, succinic acid or a mixtures of these two acids.

Where the composition of the invention is an aliphatic tricarboxylic acid as component (iv), this acid may preferably be selected from the group consisting of citric acid, isocitric acid, and also, in each case, their salts and anhydrides. Present with particular preference as tricarboxylic acid of component (iv) is citric acid.

If the composition of the invention includes as component (iv) an aromatic dicarboxylic acid or anhydride thereof, this acid or anhydride may preferably be selected from the group consisting of phthalic acid, phthalic anhydride, isophthalic acid, and terephthalic acid. Present with particular preference as aromatic dicarboxylic acid of component (iv) or anhydride thereof is phthalic acid, phthalic anhydride or a mixture thereof.

Where the composition of the invention includes an aldehydic acid as component (iv), this acid is preferably glyoxylic acid.

Where an acids of component (iv) in the form of its salt, salts contemplated are, in particular, salts of the alkali metals such as sodium and potassium, for example, and of the alkaline earth metals such as calcium and magnesium, for example, but also ammonium salts, more particularly those of type $[NH_xR_{4-x}]^+$, in which x=0, 1, 2, 3, or 4 and R is a linear or branched $C_{1-4}$ alkyl radical.

In still another embodiment, the particulate composition comprises (i) urea; and an additive comprising component (ii) and one or both of components (iii) and (iv): (ii) combination of polyethylenimine and polyvinylamine; (iii) ethanedial and/or glutaraldehyde; and (iv) at least one compound selected from the group consisting of oxalic acid, succinic acid, citric acid, phthalic acid, phthalic anhydride, glyoxylic acid, and salts thereof, where the weight fraction of component (i) is >97 wt % and the weight fraction of the sum of components (ii), (iii), and (iv) in the composition is <1 wt %.

Still yet another embodiment of the particulate composition comprise (i) urea; and an additive selected from group (a)-(i):
(a) additive comprising (ii) a combination of polyethylenimine and polyvinylamine;
(b) additive comprising (iii) glutaraldehyde;
(c) additive comprising (ii) a combination of polyethylenimine and polyvinylamine and (iv) oxalic acid;
(d) additive comprising (ii) a combination of polyethylenimine and polyvinylamine and (iv) citric acid;
(e) additive comprising (ii) a combination of polyethylenimine and polyvinylamine and (iv) succinic acid;
(f) additive comprising (ii) a combination of polyethylenimine and polyvinylamine and (iv) phthalic acid;
(g) additive comprising (ii) a combination of polyethylenimine and polyvinylamine and (iv) phthalic anhydride;
(h) additive comprising (ii) a combination of polyethylenimine and polyvinylamine and (iv) glutaraldehyde;
(i) additive comprising (ii) a combination of polyethylenimine and polyvinylamine and (iv) glyoxylic acid;
where the weight fraction of component (i) is >97 wt % and the weight fraction of the sum of components (ii), (iii), and (iv) in the composition is <1 wt %.

The weight fraction of component (i) in the particulate composition is preferably >97 wt %, more preferably >98 wt %, very preferably >98.5 wt %.

The weight fraction of the additive component may vary, depending for example on the components (ii), (iii), and (iv) used. Preferably the weight fraction of the sum of components (ii), (iii), and (iv) in the particulate composition is <0.5 wt %, more preferably <0.4 wt %, very preferably <0.3 wt %, and even more preferably <0.25 wt %.

Where the additive component comprises two or more components, their relative fractions may also vary. Thus, for example, the weight ratio of components (ii) and (iii) or the weight ratio of components (ii) and (iv) may be in the range from 1:20 to 20:1, preferably from 1:15 to 15:1, more preferably 1:10 to 10:1, and may encompass incremental values in between.

One embodiment of the particulate composition comprises a combination of polyethylenimine and polyvinylamine. The weight ratio of polyethylenimine and polyvinylamine within the combination of these two components may vary, as for example in the range from 1:20 to 20:1, preferably from 1:15 to 15:1, more preferably 1:10 to 10:1, and may comprise incremental values in between.

Furthermore, the weight ratio of the combination of the two components polyethylenimine and polyvinylamine to component (iii), or the weight ratio of the combination of the two components polyethylenimine and polyvinylamine to component (iv), may also vary and may in each case for example in the range from 1:20 to 20:1, preferably from 1:15 to 15:1, more preferably 1:10 to 10:1, and may comprise incremental values in between.

In one embodiment, the particulate composition of the invention is substantially free from formaldehyde. The expression "substantially free from formaldehyde" means for the purposes of the present invention that the composition contains <0.1 wt %, preferably <0.05 wt %, more preferably <0.005 wt %, and even more preferably <0.0005 wt % of formaldehyde.

A further aspect of the present invention relates to the use of an additive as described above for producing a particulate composition comprising urea.

All embodiments described above in connection with the particulate composition of the invention are valid correspondingly as well for the use of the additive, in accordance with the invention, for producing a particulate composition comprising urea, and are therefore not repeated at this point.

A further aspect of the invention relates to a method for producing a particulate composition comprising urea, comprising the steps of (A) providing a urea-containing solution; and (B) granulating the urea-containing solution with addition of an additive having a composition as described above.

All embodiments described above in connection with the particulate composition of the invention are valid correspondingly as well for the method of the invention for producing a particulate composition comprising urea, and are therefore not repeated at this point.

In one embodiment of the method of the invention, the urea content of the solution used in step (A) is >60 wt %, preferably >95 wt %, more preferably >97 wt %, very preferably >98 wt %, even more preferably >98.5 wt %.

The granulating of the urea-containing solution, with addition of an additive, as per step (B), may take place in accordance with customary techniques known to the skilled person, as for example by spray crystallization (prilling), drum granulation or fluidized-bed granulation.

In one embodiment of the method of the invention, the granulation in step (B) takes place by means fluidized-bed granulation, comprising the steps of
(B1) providing urea-containing seeds;
(B2) fluidizing the urea-containing seeds; and
(B3) spraying on the urea-containing solution using an additive having a composition as described above.

Where the additive comprises two or more components, they may each be used individually or together, or else in the form of premixes, in the method of the invention. The times and addition of the components may vary. Thus it is possible, for example, for one or more of the components to be added to the urea solution provided, or else for one or more of the components not to be added to the urea-containing solution until immediately before said solution is applied by spraying. Depending on the nature of the components, it may be advantageous to use them in the form of solutions, suspensions, emulsions or the like. Suitable liquids contemplated for the solutions or other formulations include, in particular, water, but also organic solvents such as, for example, alcohols, ethers, etc.

The temperature of the urea-containing solution is preferably >130° C.

In one embodiment of the invention, the method further comprises step (C): (C) separating the particulate urea composition after its production into three fractions separated, where: one fraction (F1) contains particles having the desired target size, one fraction (F2) contains particles having a size above the desired target size, and one fraction (F3) contains particles having a size below the desired target size, and wherein preferably the fraction F2, after comminution of the particles, and the fraction F3 is returned to the proceedings.

In plants for the production of the urea and its further processing into particulate compositions, ammonia is customarily also obtained. This ammonia can be converted by scrubbing with suitable acids, such as nitric acid or sulfuric acid, for example, into the corresponding ammonium salts, such as ammonium nitrate or ammonium sulfate, for example, which can be supplied for further use, in fertilizers, for example. Suitable methods and implementation of the acid scrub are described for example in WO2010/060535.

In a further embodiment, the method of the invention comprises step (D): (D) acid scrubbing. The acid scrubbing may advantageously also be accomplished using the above-described acids of component (iv), and so the resulting salts can then be utilized as component (iv) in the additive used in accordance with the invention.

A further aspect of the present invention relates to a particulate composition obtainable by a method of the invention as described above.

A still further aspect of the present invention is the use of a particulate urea composition as described above as fertilizer, as technical urea, or as feed additive, more particularly as feed additive for ruminants such as cattle, for example.

A further aspect of the invention relates to apparatus for producing a particulate composition comprising urea, comprising: (a) a granulator; (b) at least one means for adding an additive as described above; (c) at least one means for separating the particulate composition into fractions of different particle size; and (d) optionally at least one means for implementing an acid scrub.

In one embodiment of the apparatus of the invention, the granulator (a) is a fluidized-bed granulator.

The apparatus of the invention is particularly suitable for implementing the method of the invention. A further aspect of the invention therefore relates to the use of the apparatus of the invention for implementing the method of the invention for producing a particulate composition comprising urea.

The methods of the invention and the apparatus of the invention may be combined, for example, with a plant for producing urea.

The invention is elucidated below using examples. These elucidations are merely exemplary and do not restrict the general concept of the invention.

EXAMPLES

Example 1

In an experimental plant, urea was granulated in a fluidized bed granulator having a cylindrical fluidized bed 40 cm in diameter at a temperature of around 108° C. The end of the fluidized bed on the lower side was formed by a perforated plate whose holes had a diameter of 2.0 mm. The fluidizing air entered the fluidized bed with a superficial velocity of around 2 m/s. An overflow was positioned 10 cm above the bottom plate on the side wall of the bed. A defined quantity (around 45 kg) of urea particles or urea granules having a narrow size distribution was then added to the column of the granulator as seeds for the granulation. The bed with the seeds (around 50 cm in depth) was fluidized using hot air at a temperature of around 100° C., and the addition of 96 to 97 wt % strength urea solution with a temperature of around 135° C. was commenced as soon as the bed had reached the temperature of around 108° C. intended for the run. Then, from a reservoir tank, the urea solution, having a water content of 3-4 wt %, was introduced into the fluidized bed granulator at a rate of 350 kg/h via a spraying nozzle, which was operated at a temperature of around 140° C. with air, supplied at a rate of 240 kg/h. The granulating additives used in accordance with Table 1 below were then mixed with the urea solution at around 135°. Solids were removed from the fluidized bed via an outlet at regular intervals of 5 minutes, in order to maintain a substantially constant bed height. The samples of the solids thus withdrawn were then sieved in order to determine their size distribution. No solids were returned to the fluidized bed granulator. The duration per batch was in each case around 30 minutes. After the end of this time, the supply was discontinued, the granules were cooled to around 100° C. and removed from the fluidized bed granulator, and sieving took place to separate the granules into the various fractions. The fraction having the desired size distribution was then cooled to around 60° C. for analysis of its product properties. All of the fractions were weighed, in order to determine the growth rate of the granules. Furthermore, the dust from the bag filters of the outgoing air apparatus was also collected and weighed.

In accordance with the procedure described above, comparative granulator experiments were also carried out, without addition of additive and also with polyvinylamine (PVA), with a polyvinylamine/polyethylenimine mixture or with a standard additive (urea-formaldehyde additive UF80), with the granules obtained in each case being worked up and analyzed correspondingly.

Table 1a below shows the corresponding assessment of the granules in respect of dusting, compressive strength, density, and caking. The dusting sensitivity likewise indicated is the result of a visual appraisal of dust collected from a small fluidized bed cooler. The scale used for the evaluation of the granules obtained is shown in Table 1b.

TABLE 1a

| Additive | | — | UF80 | PVA | PEI/ PVA 95/5 wt %[1)] | PEI/PVA/ oxalic acid 5/90/5 wt %[2)] | Glutar- alde- hyde |
|---|---|---|---|---|---|---|---|
| Inventive (I)/ comparative (C) | | C | C | C | I | I | I |
| Metering mg/kg | | 0 | 5500 | 500 | 800 | 500 | 2500 |
| Parameter | good means | | | | | | |
| Dust in granulator filter | low | 5 | 2 | 5 | 3 | 2 | 2 |
| Dusting cooling | low | 5 | 2 | 4 | 2 | 3 | 1 |
| Caking % | none | 2 | 1 | 3 | 1 | 2 | 1 |
| Cake hardness | FF | 3 | 1 | 3 | 1 | 1 | 1 |
| Compressive strength | high | 4 | 2 | 3 | 3 | 2 | 1 |
| Bulk density (uncompacted) | high | 3 | 1 | 3 | 1 | 1 | 3 |
| Assessment (not weighted) | | 22 | 9 | 21 | 11 | 11 | 9 |

PVA: polyvinylamine
PEI: polyethylenimine
[1)]based in each case on the mixture of PVA and PEI
[2)]based in each case on the mixture of PVA, PEI and oxalic acid TABLE 1b

| Scale | Dust in filter (%) | Dust cooling | Compressive strength kg | Bulk density (g/l) | Caking (%) | Hardness (kg) |
|---|---|---|---|---|---|---|
| 1 | 0-4 | 0 | >3.5 | >675 | 0 | no |
| 2 | >4-6 | 1 | >3.0-3.5 | 675-665 | 0-10 | low |
| 3 | >6-8 | 2 | >2.5-3.0 | <665-655 | 11-20 | moderate |
| 4 | >8-10 | 2-3 | >2.0-2.5 | <655-645 | 21-30 | hard |
| 5 | >10 | 3 | <2.0 | <645 | >30 | |

Example 2

In accordance with the procedure described in Example 1, the effect of a granulating additive of the invention, comprising oxalic acid, metered at various levels, and of a mixture of 500 mg/kg of polyethyleneiminine and polyvinylamine (40 wt %/60 wt %, based in each case on the mixture of polyethylenimine and polyvinylamine) was ascertained. In this case the oxalic acid was added to the urea solution reservoir tank, and the polyethyleniminine/polyvinylamine mixture was supplied to the stream of urea fed to the nozzle, prior to spraying. The resulting urea solution, having a water content of 3 wt %, was then supplied at a temperature of 132° C. and a rate of 350 kg/h, and the product was worked up as described in Example 1. A corresponding comparative experiment with formaldehyde was likewise carried out.

Table 2 below shows in each case the fraction of dust in the fluidized bed granulator:

TABLE 2

| | Inventive (I)/ comparative (C) | Metering in mg/kg | Dust fraction/ granulator in % |
|---|---|---|---|
| Oxalic acid | I | 0 | 5.19 |
| | I | 250 | 4.44 |
| | I | 500 | 4.05 |
| | I | 1000 | 2.81 |
| Formaldehyde | C | 4500 | 3.9 |

Example 3

In accordance with the procedure described in Example 1, the effect of granulating additives of the invention consisting of a mixture of 500 mg/kg of polyethyleniminine and polyvinylamine (40 wt %/60 wt %, based in each case on the mixture of polyethylenimine and polyvinylamine) with oxalic acid, citric acid, succinic acid, phthalic acid, phthalic anhydride, glutaraldehyde, and glyoxylic acid on the granulating of urea was ascertained. Oxalic acid, citric acid, succinic acid, phthalic acid, phthalic anhydride and glutaraldehyde were each added to the urea reservoir, while the glyoxylic acid and also the mixture of polyethyleniminine and polyvinylamine was added to the stream of urea fed to the nozzle, in each case prior to spraying. Here again, the resulting urea solution, having a water content of 3 wt %, was then supplied at a temperature of 132° C. and a rate of 350 kg/h, and the product was worked up as described in Example 1. A corresponding comparative experiment with formaldehyde was likewise carried out.

| | Inventive (I)/ comparative (C) | Metering (mg/kg) | Compressive strength (in kg) | Dusting (in %) |
|---|---|---|---|---|
| No additive | C | 0 | 2.26 | 10.85 |
| Formaldehyde | C | 4500 | 3.75 | 3.90 |
| Oxalic acid | I | 1000 | 4.48 | 2.81 |
| Citric acid | I | 1000 | 4.05 | 4.44 |
| Succinic acid | I | 1000 | 3.63 | 3.70 |
| Phthalic acid | I | 1000 | 3.84 | 3.70 |
| Phthalic anhydride | I | 1000 | 4.72 | 2.48 |
| Glutaraldehyde | I | 1000 | 3.71 | 3.65 |
| Glyoxylic acid | I | 1500 | 5.07 | 2.74 |

The investigations of the granules obtained according to Examples 1-3 showed that both dusting and the properties of the granules (compressive strength, caking tendency) improved on addition of the additives of the invention. The result was comparable with or even better than the results obtained when using formaldehyde, with substantially smaller quantities of additive being required.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. It will be understood that certain features and subcombinations are of utility and may be employed without reference to other features and subcombinations and are contemplated within the scope of the claims. The specific configurations and contours set forth in the accompanying drawings are illustrative and not limiting. All steps need not be performed in the order shown or described.

The invention claimed is:

1. A particulate composition comprising
   (i) urea;
   and an additive comprising component (ii) and at least one of components (iii) and (iv):
   (ii) a combination of polyethylenimine and polyvinyl alcohol or a combination of polyethylenimine and polyvinylamine;
   (iii) at least one aliphatic $C_2$-$C_8$ dialdehyde; and
   (iv) at least one compound selected from the group of aliphatic dixcarboxylic acids, their salts and anhydrides, aliphatic tricarboxylic acids, their salts and anhydrides, aromatic dicarboxylic acids, their salts and anhydrides, and aldehydic acids, their salts and anhydrides;
   where the weight fraction of component (i) is >60 wt % and the weight fraction of the sum of components (ii) and (iii) in the composition is <1 wt %.

2. The particulate composition of claim 1, comprising
   (i) urea;
   and an additive comprising component (ii) and one or both of components (iii) and (iv):
   (ii) a combination of polyethylenimine and polyvinylamine;
   (iii) ethanedial and/or glutaraldehyde;
   (iv) at least one compound selected from the group consisting of oxalic acid, succinic acid, citric acid, phthalic acid, phthalic anhydride, glyoxylic acid, and salts thereof, where the weight fraction of component (i) is >97 wt % and the weight fraction of the sum of components (ii), (iii), and (iv) in the composition is <1 wt %.

3. The particulate composition of claim 2, wherein the polyethylenimine of component (ii) has a molecular weight in the range of 500-2 000 000 Da.

4. The particulate composition of claim 3, wherein the polyvinylamine of component (ii) has a molecular weight in the range of 500-1 000 000 Da.

5. The particulate composition of claim 1, wherein the weight fraction of component (i) in the composition is >98 wt %.

6. The particulate composition of claim 1, wherein the weight fraction of the sum of components (ii), (iii), and (iv) in the composition is <0.5 wt %.

7. The particular composition of claim 1, wherein the weight fraction of component (i) is more than 97 wt % and the weight fraction of the sum of components (ii), (iii), and (iv) in the composition is less than 1 wt %.

8. A method for producing a particulate composition comprising urea, comprising the steps of:
   (A) providing a urea-containing solution; and
   (B) granulating the urea-containing solution with addition of an additive defined as defined in claim 1.

9. The method of claim 8, wherein the urea content of the solution is >60 wt %.

10. The method of claim 8, wherein the granulation in step (B) takes place by means of fluidized bed granulation, comprising the steps of:
    (B1) providing urea-containing seeds;
    (B2) fluidizing the urea-containing seeds;
    (B3) spraying the urea-containing solution onto the seeds, using an additive as defined in claim 1.

11. The method of claim 8, wherein the temperature of the urea-containing solution is >130° C.

12. The method of claim 8, further comprising step (C):
    (C) separating the particulate urea composition after its production into three fractions is separated, where:
        one fraction (F1) contains particles having the desired target size,
        one fraction (F2) contains particles having a size above the desired target size, and
        one fraction (F3) contains particles having a size below the desired target size.

13. The method of claim 12, further comprising step (D):
    (D) wet scrubbing.

* * * * *